United States Patent
Holmes

[11] Patent Number: 6,006,581
[45] Date of Patent: Dec. 28, 1999

[54] ROD BENDING SYSTEM

[75] Inventor: Russell P. Holmes, Boston, Mass.

[73] Assignee: Hol-Med Corporation, Easton, Mass.

[21] Appl. No.: 09/178,667

[22] Filed: Oct. 26, 1998

[51] Int. Cl.[6] .............................. B21D 7/06; H01L 21/265
[52] U.S. Cl. ............................ 72/458; 72/213; 72/409.1; 140/106
[58] Field of Search .............................. 72/212, 213, 457, 72/458, 389.1, 409.1; 140/106

[56] References Cited

U.S. PATENT DOCUMENTS

| | | | |
|---|---|---|---|
| 3,732,721 | 5/1973 | Cusimano | 72/458 |
| 4,594,875 | 6/1986 | Schweitzer | 72/389 |
| 5,490,409 | 2/1996 | Weber | 72/458 |
| 5,819,580 | 10/1998 | Gauthier | 72/458 |
| 5,890,390 | 4/1999 | Throssel | 72/458 |

*Primary Examiner*—David Jones
*Attorney, Agent, or Firm*—Cesari and McKenna, LLP

[57] ABSTRACT

A rod bending system includes a handle that holds a template rod and an implant rod in close proximity and in a fixed orientation with respect to one another. The system further includes one or more of the following: (a) a rod bender for bending the implant rod, the rod bender including a central pivot that is dimensioned and contoured to fit between the two rods; (b) a guide that slideably attaches to the template rod and clips onto the implant rod, the guide sliding along regions of the rods that correspond and stopping at regions that diverge; and (c) a stand that includes a holder which retains the handle at a desired orientation and a pedestal that elevates the handle above a supporting surface.

20 Claims, 4 Drawing Sheets

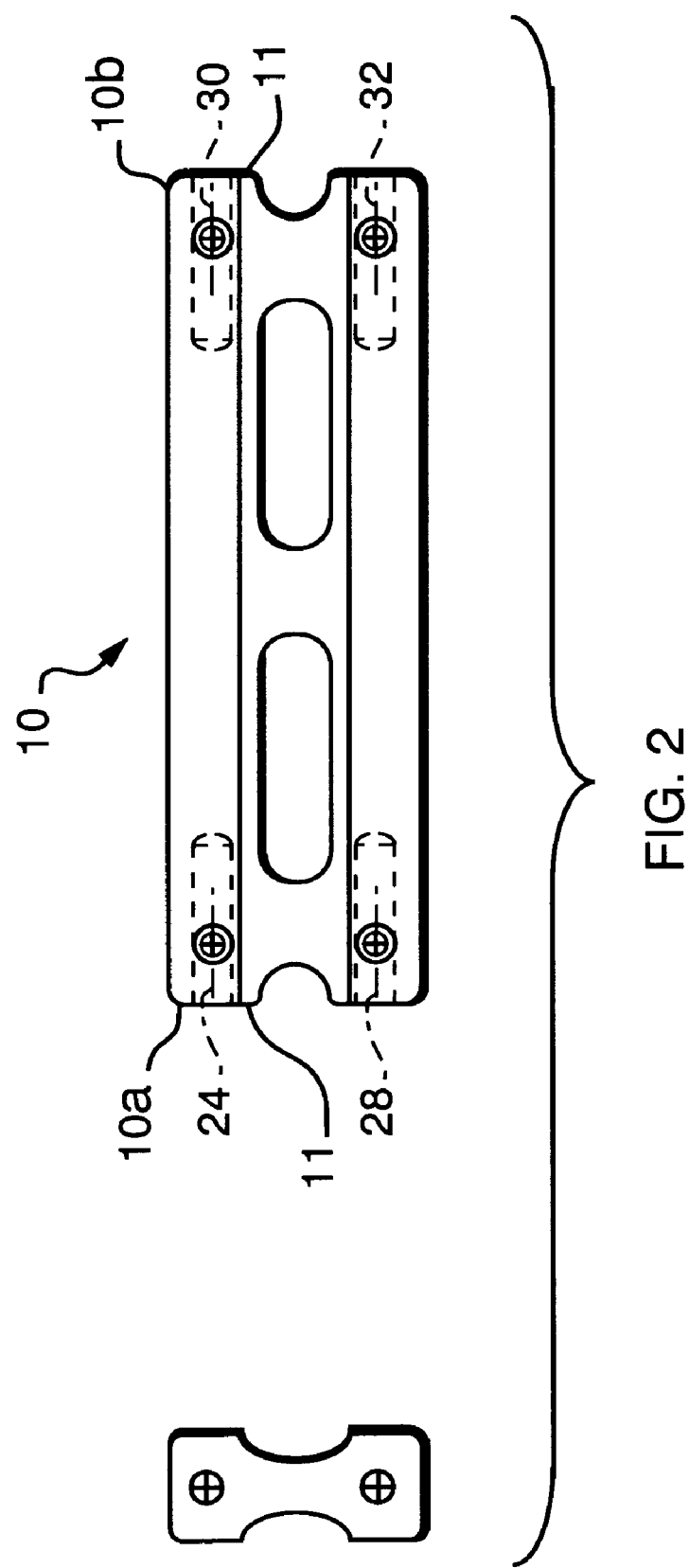

ROD BENDING SYSTEM

FIELD OF INVENTION

The invention relates generally to medical instruments and, in particular, to instruments for bending surgically implantable rods.

BACKGROUND OF THE INVENTION

To promote bone growth that will strengthen and straighten a spine that is curved as a result of, for example, scoliosis, surgeons may implant a shaped rod next to the spine. The rod must be shaped appropriately for each patient, based on the severity and direction of the curvature of the spine. For accuracy, the surgeon shapes the rod after exposing the spine.

As the surgeon views the exposed spine, he or she may bend the implant rod to the desired shape free-hand, using a conventional rod bender. Alternatively, the surgeon may first bend a pliable template rod by hand to the desired shape, and thereafter use a conventional rod bender to bend the implant rod to correspond to the shape of the template rod. An example of the conventional rod bender is the three-point rod bender discussed in U.S. Pat. No. 4,474,046.

The invention relates to the rod-bending method that includes the use of the template rod. Conventional template rods are marked with a line that signifies the orientation of the rod. Typically, the line faces up as the surgeon begins bending the template rod to fit the patient. Using conventional tools, the implantable rod, which is made of stainless steel or titanium and not easily bent, is placed in a rod holder. The surgeon makes bends in the implant rod that correspond to the bends in the template rod, using the line in the template rod as a visual guide to the required direction and degree of bending.

Generally, the surgeon works with a trained assistant who holds the implant rod at desired orientations while the surgeon positions the rod bender along the rod to make the appropriate bends. The assistant must position the implant rod at the appropriate orientation and then hold the rod securely, avoiding moving the rod laterally and/or rotating the rod while the rod is being bent. As the surgeon bends the implant rod, he or she visually compares the rod with the template rod, to determine if the two rods correspond in shape. The visual comparison must be made in three dimensions, to ensure that the implant rod conforms to all of the bends and displacements of the template rod.

The conventional rod-bending procedure is time consuming, and there is much room for error. For example, an assistant may incorrectly position the implant rod or allow the implant rod to move laterally or rotate while it is being bent, and the implant rod is thus bent incorrectly. The rod must then be re-bent, to correct its shape. Re-bending the rod may cause unnecessary scarring of the implant rod or it may weaken the rod, which leaves the rod prone to stress fractures. If the rod cannot be re-bent to the appropriate shape, a new rod must be started. The re-bending of the old rod or the starting a new rod takes time, and thus, prolongs the surgical procedure. Alternatively, the surgeon may incorrectly determine, through the visual comparison, that the two rods correspond. The result may then be an implant rod that does not conform to the template rod over its entire length, that is, a rod that may not be optimally shaped for the patient.

SUMMARY OF THE INVENTION

The invention is a rod bending system that includes a novel handle, which securely holds the shaped template rod in close proximity to and in the same orientation as the implant rod. The surgeon can then rotate and bend the implant rod, as appropriate, without either rod being unintentionally moved or rotated relative to the other. The close proximity of the rods promotes more accurate visual comparison.

The system also includes an improved three-point rod bender that includes pivots that are dimensioned, contoured and positioned such that the handle with the two rods can be rotated about the bender. This allows the implant rod to be rotated to a desired orientation relative to the pivots of the rod bender, such that the rod can then be appropriately bent. The system further includes a guide that attaches to the template rod and clips onto the implant rod. The guide can be moved along the two rods, to check that the bends and twists of the two rods correspond over their entire lengths. A stand that is included in the system retains the handle, and thus, the two rods, at any desired orientation and at a predetermined height above, for example, a table. The handle rotates in the stand, under the control of the surgeon, to re-orient the rods relative to the rod bender before a next bend is made in the implant rod.

The individual components of the system may be advantageously used all together or in various combinations, to achieve some or all of the desired results.

More specifically, the handle holds one end of each of the template rod and the implant rod close together, approximately 0.75 of an inch apart, and retains the rods at the same lateral position and orientation relative to one another throughout the bending process. The surgeon may thus re-orient the handle without adversely affecting the relative alignment of the rods, so that he or she can bend the implant rod in a particular direction without changing the orientation of the bender. As discussed in more detail below, the handle is contoured such that the rod bender can operate as closely as possible to the end of the implant rod that is held by the handle.

The improved rod bender includes pivots that are positioned and dimensioned such that the template rod can rotate through a maximum arch around the outer pivots, while the implant rod is correspondingly rotated relative to the central pivot. The central pivot, which is the point about which the rod bends, is also contoured so that it fits between the two rods and still presents a predetermined radius to the implant rod.

The guide is constructed with a hole that slides over the template rod and an appropriately spaced C-shaped opening that clips onto the implant rod. The guide thus moves along the implant rod as it slides along the template rod, and gauges the correspondence between the two rods in three dimensions along their entire lengths.

The stand is shaped to retain the handle, with the rods projecting therefrom, at any desired orientation. The stand prevents unintended movement or rotation of the rods throughout the bending process, and eliminates the need for an assistant who is specifically trained to manipulate the implant rod. The stand thus makes the bending process both more economical and, by giving the surgeon complete control over the orientation of the implant rod, more predictable.

By using some or all of the tools described above, a surgeon can accurately bend an implant rod to conform to the template rod, without having to re-bend the rod to compensate for unintended movement or rotation of the implant rod. As discussed, the improved rod bender has an overall design that is familiar to most surgeons, and yet, it is contoured and dimensioned to allow the template and implant rods that are held in the handle to rotate freely relative to the rod bender. The handle ensures that the two rods remain stationary relative to one another, and in close proximity for visual comparison. The guide ensures that the implant rod corresponds to the template rod over its entire length. Each tool alone, and/or the entire system operating together, reduces the time required to produce a correctly bent implant rod, which translates directly to an overall reduction in the length of the surgically procedure.

DESCRIPTION OF THE DRAWINGS

FIG. 2 depicts the handle of FIG. 1 in more detail;

DETAILED DESCRIPTION OF AN ILLUSTRATIVE EMBODIMENT

Figure 1:
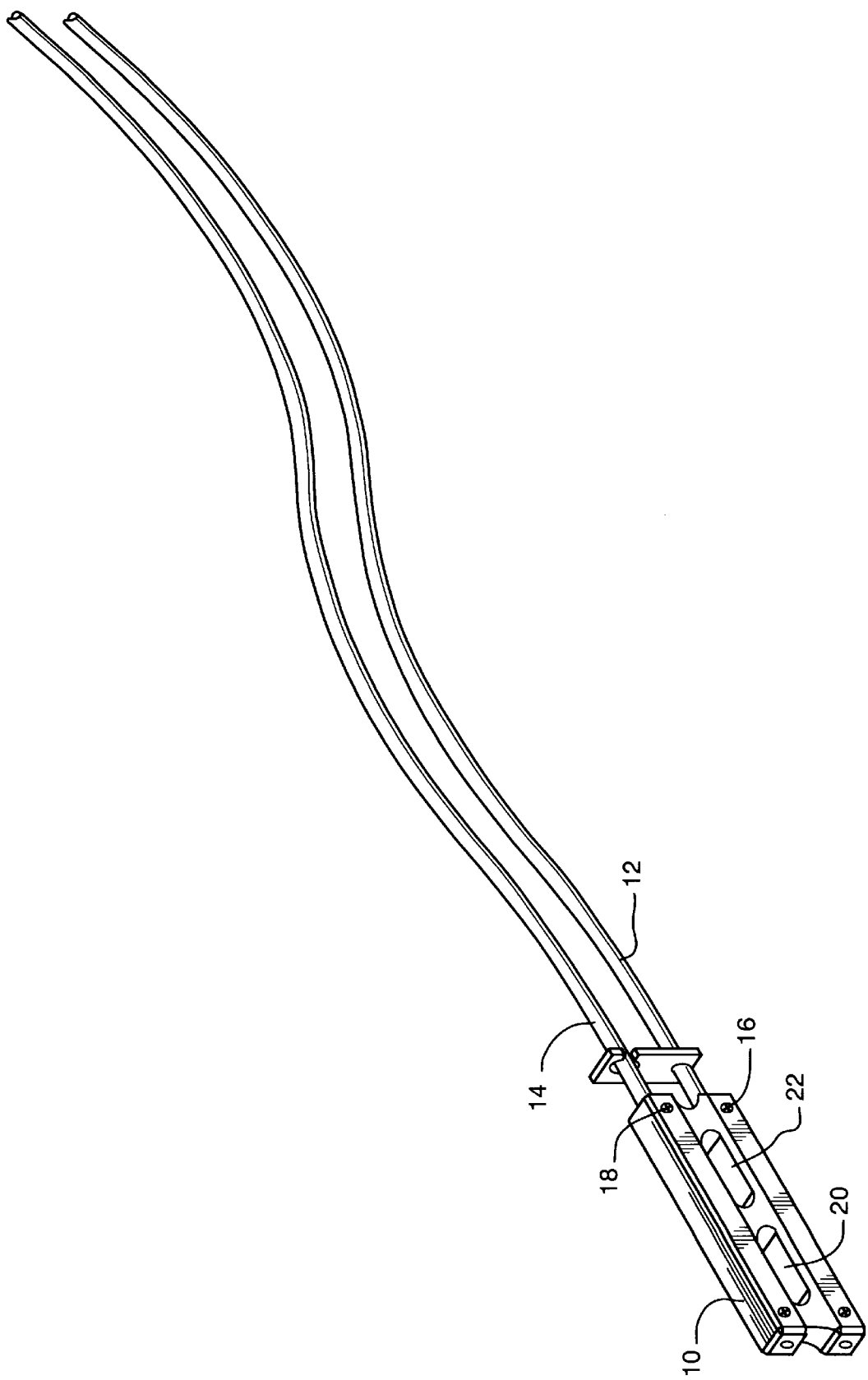
FIG. 1 depicts a template rod and an implant rod held in close proximity by a handle.

Referring now to FIG. 1, a handle 10 holds a template rod 12 and an implant rod 14 in close proximity and in a fixed orientation relative to one another. Screws 16 and 18 retain the ends of the rods in place within the handle, such that the implant rod 14 can be bent and twisted without moving laterally or rotating relative to the template rod 12. The handle 10 is preferably made of stainless steel, and includes cut-outs 20 and 22 to reduce its weight.

As shown in more detail in FIG. 2, slots 24 and 28 on one end 10a of the handle hold rods that are relatively small in diameter, e.g. 0.187 of an inch. Larger slots 30 and 32 on an opposite end 10b of the handle hold rods that are larger in diameter, e.g. 0.250 of an inch. The handle 10 can thus be used with the two most common sizes of implant rods.

The center spans 11 of the ends 10a and 10b of the handle, that is, the areas between the slots 24 and 28 or 30 and 32, are contoured inwardly such that an outer pivot of a rod bender 40 (FIG. 3) can be positioned relatively close to the end of the implant rod 14. This allows the rod to be bent essentially from the point at which the rod emerges from the handle.

Figure 3A:
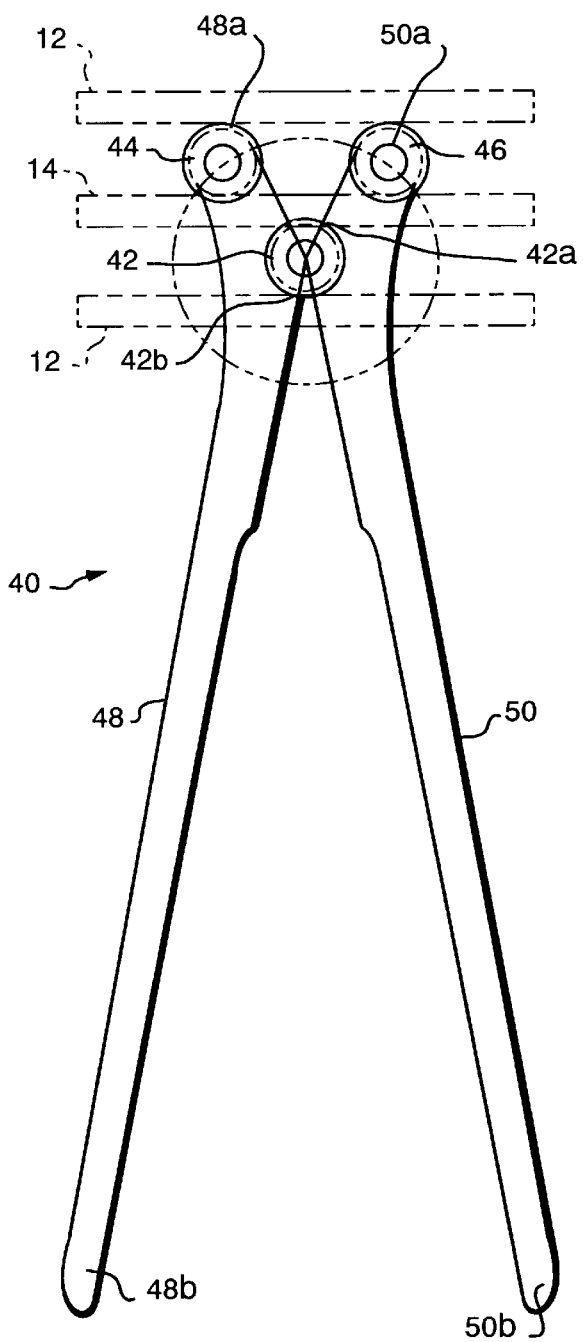
FIGS. 3A–B depict an improved rod bender for bending the implant rod depicted in FIG. 1.
Figure 3B:
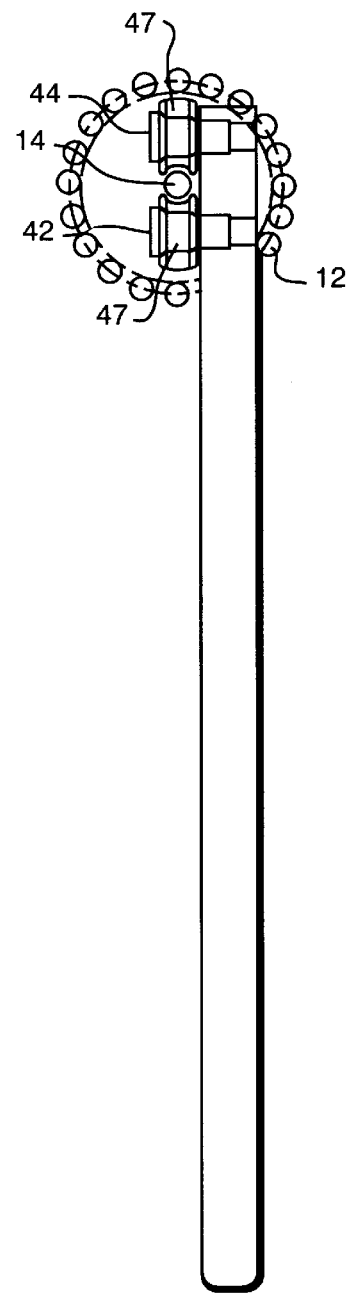

Referring now also to FIGS. 3A–B, the rod bender 40, which is designed specifically for use with rods that are held in the handle 10, includes three points, or pivots, namely, a central pivot 42 and two outer pivots 44 and 46. As shown in relief in FIG. 3A, the implant rod 14 fits between the center pivot 42 and the two outer pivots 44 and 46, and bends about the center pivot. As in a conventional rod bender, the outer pivot 44 is at the end 48a of a handle 48, while the outer pivot 46 is at the end 50a of a handle 50, with the handles 48 and 50 held together by the center pivot 44 which extends through corresponding holes (not shown) in the handles.

When the ends 48b and 50b handles 48 and 50 are separated, that is, when the bender is in the open position, the implant rod 14 extends between the center and the two outer pivots. The ends 48b and 50b of the handles are then squeezed inwardly, that is, together, to bend the rod to a desired angle around the center pivot 42. The implant rod 14 is made of steel or titanium, and thus, a relatively large force is required to squeeze the handles 48 and 50 together to bend the rod.

As depicted in FIG. 3A, the outer pivots 44 and 46 are dimensioned and positioned relative to the center pivot 42 to fit between the implant rod 14 and the template rod 12 when the rods are held in close proximity by the handle 10 (FIG. 1). The outer pivots are thus approximately 0.70 of an inch at their outer diameter, and are spaced from the outer diameter of the center pivot by approximately 0.30 of an inch. Each pivot has an indentation 48 for receiving the rod 14. The center pivot 42 is approximately 0.80 of an inch in diameter at its widest span so that it can produce a relatively large bend in the rod. The pivot 42 is cut at an angle to flatten the bottom edge 42b and has a minimum profile, such that the pivot easily fits between the two rods 12 and 14. The pivot 42, like the outer pivots, has an indentation 48 for receiving the rod 14.

In the embodiment depicted in FIG. 3B, the template rod rotates in a 280° arch about the outer pivots 44 and 46 of the rod bender. The implant rod can thus be bent to essentially any angle while it is held by the handle at a fixed orientation relative to the template rod. The rod bender 40 is moved only laterally, that is, moved along the length of the implant rod, during the bending procedure, and the rods are rotated into appropriate positions for bending.

Alternatively, the rod bender may rotate freely about the implant rod in either direction, until the handles 48 and 50 hit the template rod. Using this method, the surgeon leaves the handle, and thus the rods, stationary and re-orients the rod bender to make the appropriate bends.

Figure 4:
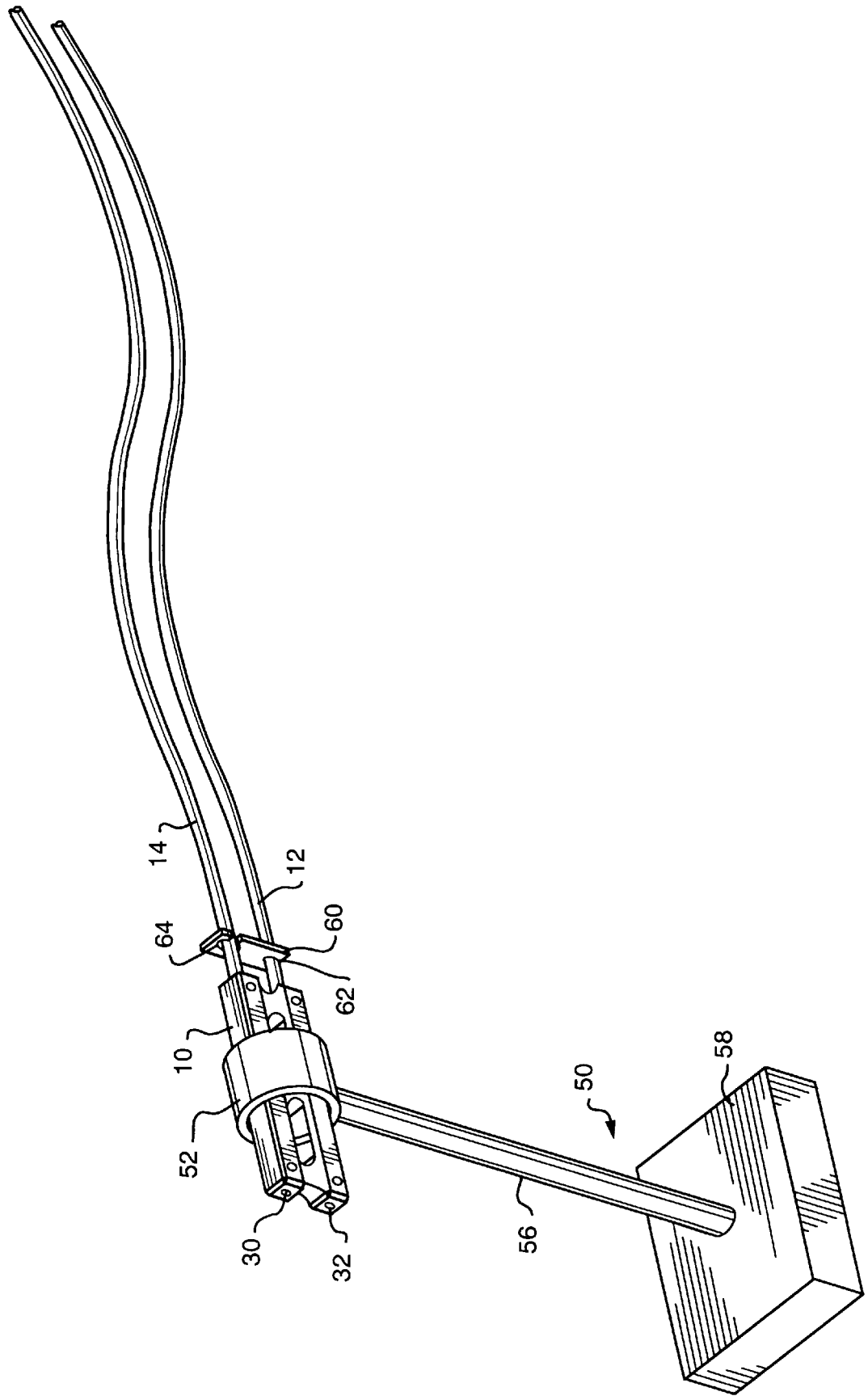
FIG. 4 depicts the handle of FIG. 1 held in place by a stand.

Referring now to FIG. 4, a stand 50 includes an open-ended holder 52 that is shaped to receive the handle 10, and a pedestal 56 and a base 58 that position the holder at a predetermined height above a supporting surface (not shown). The holder 52 is dimensioned such that an end 10a or 10b of the handle 10 can be pushed, with some effort, through one open end 54 and out the other open-end 56. The weight of the handle 10 and the interaction between the edges 11 of the handle 10 and the inner surface 53 of the holder 52 retain the handle in a desired orientation. An optional stop (not shown) may be included on the handle and corresponding indents (not shown) included in the holder to aid in the positioning of the handle.

During a rod bending procedure, the surgeon rotates the handle 10, to position the rod for bending. Once the handle is in position, the holder 52 retains the handle 10 in that position and prevents it from moving laterally or rotating while the implant rod 14 is being bent. In the embodiment depicted in FIG. 4, the holder 52 is circular, which allows the handle to be rotated by the surgeon to any desired orientation before each bend is made.

The stand replaces the trained assistant, who must otherwise manipulate the implant rod in accordance with the surgeon's instructions. The stand adds predictability, since it allows the rods to be rotated specifically to a desired orientation before bending and ensures that the rods do not move while the surgeon makes the bend in the implant rod. Also, the stand is relatively inexpensive to manufacture, and is thus less costly over time than using a specially-trained assistant for each procedure.

As also depicted in FIG. 4, a guide 60, which consists of a rectangular plastic or metal piece, is constructed with a hole 62 that slides over the template rod 12 and a closely-spaced C-shaped slot 64 that fits over the implant rod 14. The receiving end 65 of the slot 64 is wider than the implant rod, such that the correspondence between the two rods can be gauged as the guide is moved laterally along the rods. The guide may include markings (not shown) along the end 65 of the slot 64, to indicate the degree of correspondence.

As the implant rod 14 is bent to the shape of the template rod 12, the guide is moved along the two rods to determine the correspondence between them. If the implant rod is not bent to a shape that is essentially the same as that of the template rod, the guide stops at the point at which the shapes of the two rods diverge. The surgeon must then re-work that point and produce a bend that more closely corresponds to the bend of the template rod, in order for the guide to advance. Also, the surgeon can decide to re-work certain points or not, based on the degree of correspondence and presumably the amount of time the re-working will take. When the guide readily slides over the entire length of the rods, the surgeon knows that the implant rod essentially corresponds to the template rod. The guide 60 thus improves upon the conventional visual inspection method of comparing the rods.

The foregoing description has been limited to a specific embodiment of this invention. It will be apparent, however, that variations and modifications may be made to the invention, such as making the handle out of other materials, changing the relative positions of the slots in the handle, such that the rods are spaced more or less closely together, with corresponding changes in the size, contours and positions of the pivots of the rod bender, changing the overall shape of the guide to semi-circular, round and so forth, changing the shape of the holder in the stand such that the holder receives the handle at one of a small number of orientations, making the pedestal adjustable and/or pivotable and so forth, with the attainment of some or all of its advantages. Therefore, it is the object of the appended claims to cover all such variations and modifications as come within the true spirit and scope of the invention.

What is claimed is:

1. A rod bending system for bending an implant rod to conform to the shape of a template rod, the system including:
    A. a handle to hold the implant rod and the template rod in close proximity and in a fixed orientation relative to one another; and
    B. a three-pivot rod bender with a center pivot that is sized and contoured to fit between the two rods held by the handle.

2. The rod bending system of claim 1 wherein the rod bender includes two outer pivots that are positioned and dimensioned to fit between the two rods.

3. The rod bending system of claim 1 further including a guide that slidably attaches to the template rod and clips to the implant rod, the guide slidably moving along the lengths of the two rods when the rods conform in shape, and stopping at a point where the two rods diverge in shape.

4. The rod bending system of claim 1 further including a stand for holding the handle and at a desired orientation against unintended lateral and rotational movement.

5. The rod bending system of claim 4 wherein the stand includes:
    i. a holder for receiving and retaining the handle;
    ii. a base; and
    iii. a pedestal for elevating the holder above the base.

6. The rod bending system of claim 5 wherein the holder is circular in shape and allows the handle to be rotated to any desired orientation relative to the base.

7. The rod bending system of claim 1 wherein the handle includes a first end and a second end and at the first end has a first set of two slots that are sized to hold the two rods.

8. The rod bending system of claim 7 wherein a section of the first end of the handle that is between the two slots is contoured inwardly to provide clearance for a rod bender.

9. The rod bending system of claim 7 wherein the second end of the handle includes a second set of two slots with diameters that differ from the first set of slots.

10. The rod bending system of claim 7 wherein a section of the second end between the two slots is contoured inwardly to provide clearance for a rod bender.

11. A system for use with a rod bender, the system including:
    A. a handle to retain a template rod and an implant rod in close proximity in a fixed orientation relative to one another; and
    B. a stand to retain the handle in a desired orientation and height relative to a supporting surface.

12. The system of claim 11 wherein the handle includes a first end and a second end and at the first end a first set of two slots that are sized to hold the two rods.

13. The system of claim 12 wherein a section of the first end of the handle that is between the two slots is contoured inwardly.

14. The system of claim 12 wherein the handle includes a second end that includes a second set of slots that differ in diameter from the first set of slots.

15. The system of claim 14 wherein a section of the second end of the handle between the two slots is contoured inwardly.

16. The system of claim 11 wherein the stand includes
    i. a holder for receiving and retaining the handle;
    ii. abase; and
    iii. a pedestal for elevating the holder above the base.

17. The system of claim 11 further including a guide that slidably attaches to the template rod and clips to the implant rod, the guide slidably moving along the lengths of the two rods when the rods conform in shape, and stopping at a point where the two rods diverge in shape.

18. A handle for use in retaining an implant rod, the handle including:
    A. a slot for retaining the implant rod;
    B. a second slot that is in close proximity to the first slot for holding a template rod that is bent in the shape in which the implant rod is to be bent, the second slot holding the template rod in a fixed orientation relative to the implant rod;
    C. an end section between the two slots that is contoured inwardly to provide clearance for a rod bender that is used to bend the implant rod.

19. The handle of claim 18 further including at a second end and second set of slots that differ in diameter from the first set of slots, wherein the slots in the second set are in close proximity and receive and retain the implant rod and the template rod in a fixed position and orientation relative to one another.

20. The handle of claim 18 further including cut-outs that reduce the weight of the handle.

* * * * *